(12) United States Patent
Buist, Sr.

(10) Patent No.: US 10,631,895 B2
(45) Date of Patent: Apr. 28, 2020

(54) DENTAL CUTTING TOOL

(71) Applicant: Charles Buist, DMD, PA, Hilton Head Island, SC (US)

(72) Inventor: Charles Buist, Sr., Irmo, SC (US)

(73) Assignee: Charles Buist, DMD, PA, Hilton Head Island, SC (US)

( * ) Notice: Subject to any disclaimer, the term of this patent is extended or adjusted under 35 U.S.C. 154(b) by 125 days.

(21) Appl. No.: 15/981,964

(22) Filed: May 17, 2018

(65) Prior Publication Data

US 2019/0350613 A1  Nov. 21, 2019

(51) Int. Cl.
*A61B 17/3211* (2006.01)
*A61B 17/16* (2006.01)
*A61C 3/02* (2006.01)

(52) U.S. Cl.
CPC ...... *A61B 17/3211* (2013.01); *A61B 17/1615* (2013.01); *A61C 3/02* (2013.01)

(58) Field of Classification Search
CPC ............ A61B 17/3211; A61B 17/3213; A61B 17/1673; A61B 17/1688; A61C 3/02
USPC ........................................ 403/102, 165, 166
See application file for complete search history.

(56) References Cited

U.S. PATENT DOCUMENTS

| 2,640,379 | A | * | 6/1953 | Graves | B23B 51/00 |
| | | | | | 408/228 |
| 2,838,049 | A | * | 6/1958 | Eisenhofer | A61B 17/3211 |
| | | | | | 606/167 |
| 5,188,531 | A | | 2/1993 | Von Sutfin | |
| 5,704,740 | A | | 1/1998 | Ebenhoch et al. | |
| 6,099,310 | A | | 8/2000 | Bornstein et al. | |
| 9,079,255 | B2 | | 7/2015 | Jager et al. | |
| 9,308,587 | B2 | | 4/2016 | Kitagawa et al. | |
| 2003/0143513 | A1 | * | 7/2003 | Flanagan | A61B 17/1673 |
| | | | | | 433/141 |
| 2009/0136898 | A1 | * | 5/2009 | Kim | A61B 17/1655 |
| | | | | | 433/165 |
| 2011/0236853 | A1 | * | 9/2011 | Shimoo | A61C 3/02 |
| | | | | | 433/82 |
| 2014/0370458 | A1 | * | 12/2014 | Jeng | A61C 3/02 |
| | | | | | 433/166 |
| 2016/0367281 | A1 | | 12/2016 | Gee et al. | |

FOREIGN PATENT DOCUMENTS

CH           664279 A5    2/1988
WO   WO1994022380 A1   10/1994

* cited by examiner

*Primary Examiner* — Matthew J Lawson
(74) *Attorney, Agent, or Firm* — Burr & Forman LLP; Hunter S. Freeman

(57) ABSTRACT

An improved cutting tool is provided for cutting openings in a patient's jaw so that a dental implant may be inserted therein. The cutting tool includes a tapered pick portion that has a generally flat surface and a radiused surface. The pick portion further includes a cutting blade that extends along at least a portion of the generally flat surface of the pick portion so that the cutting blade is generally opposite from the radiused surface. When the pick portion is inserted into the patient's jaw and rotated, the radiused surface engages a first section of the patient's bone to create at least one micro fracture in the bone while the cutting blade engages a second section of the bone and removes a portion of the bone in the second section.

19 Claims, 4 Drawing Sheets

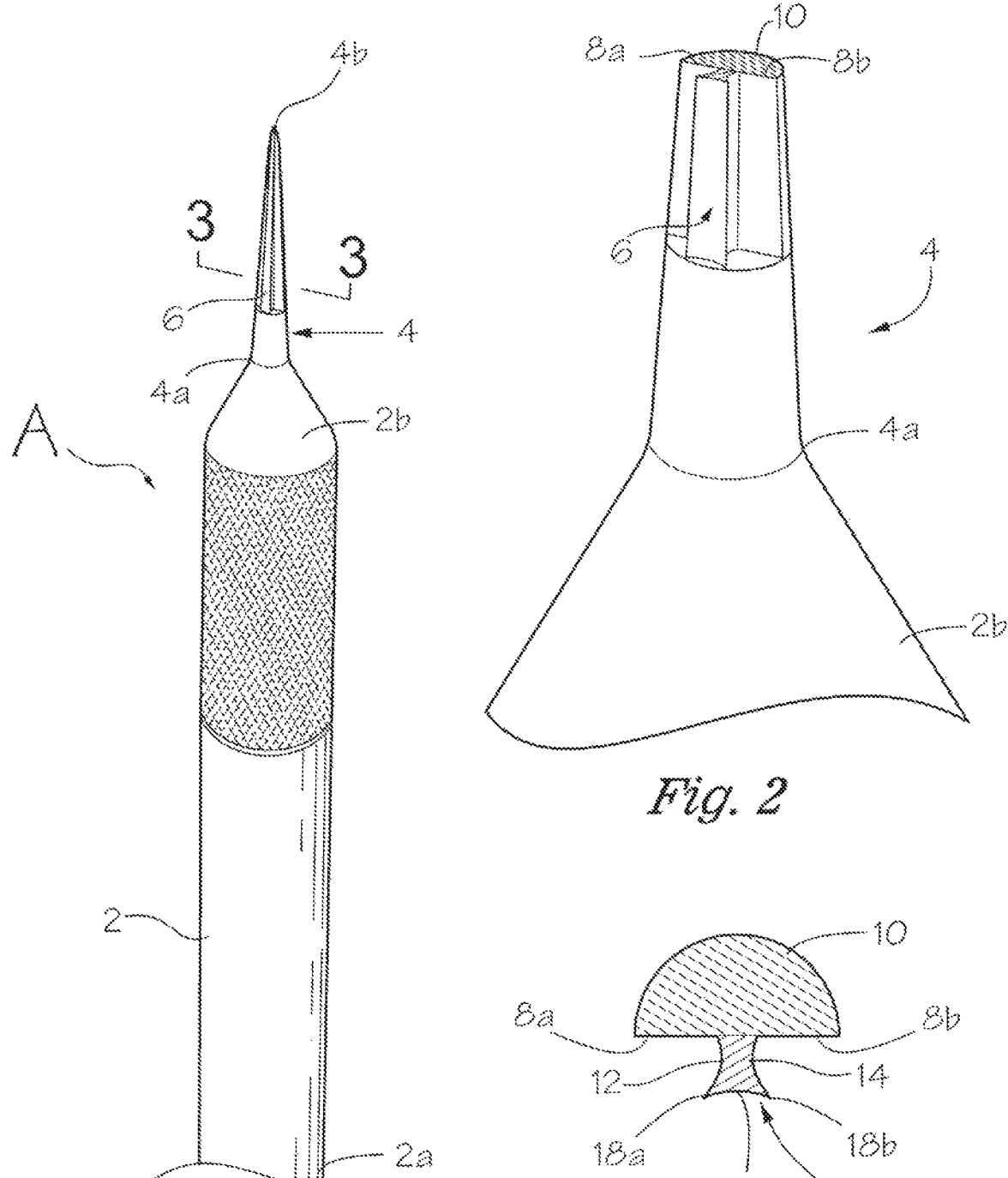

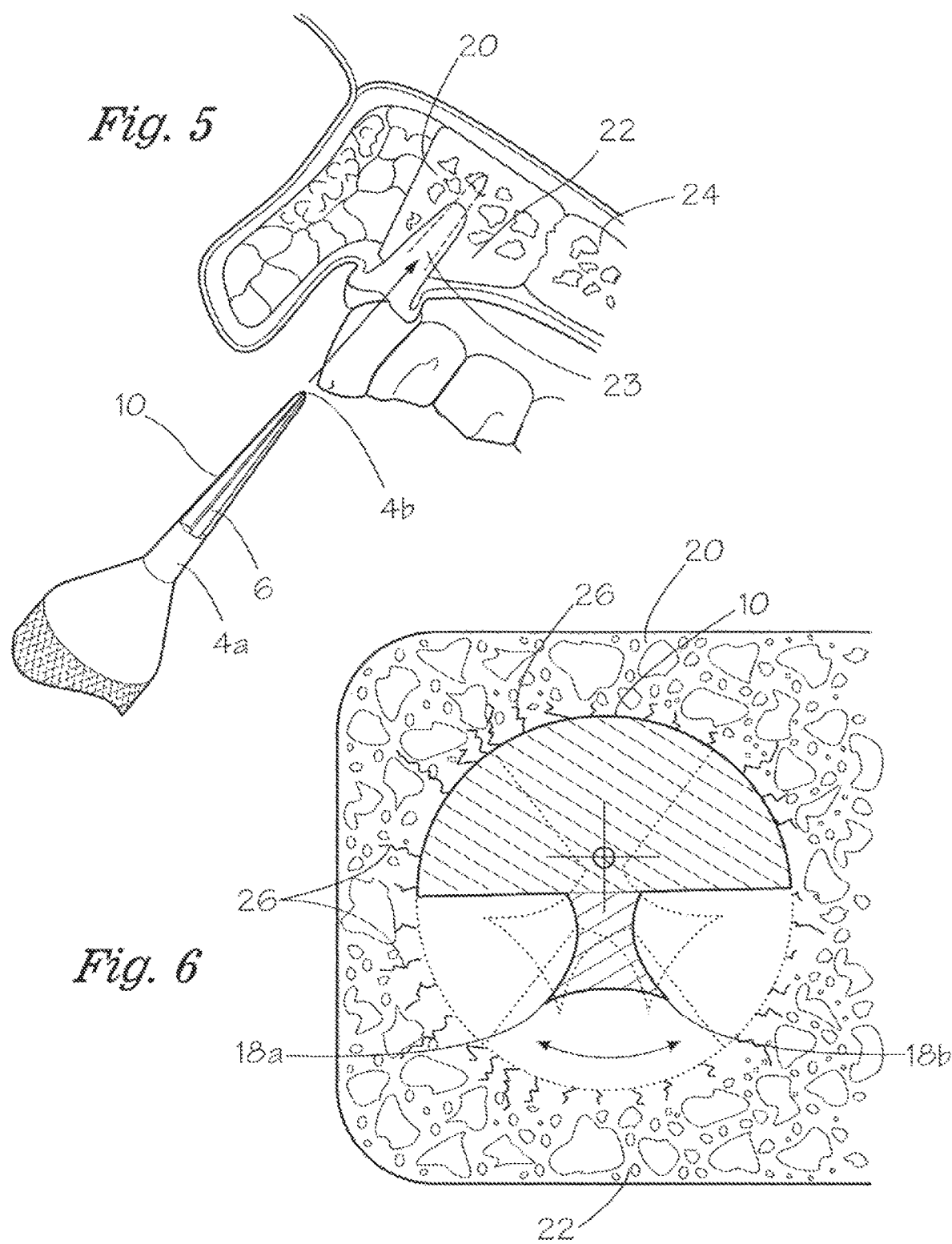

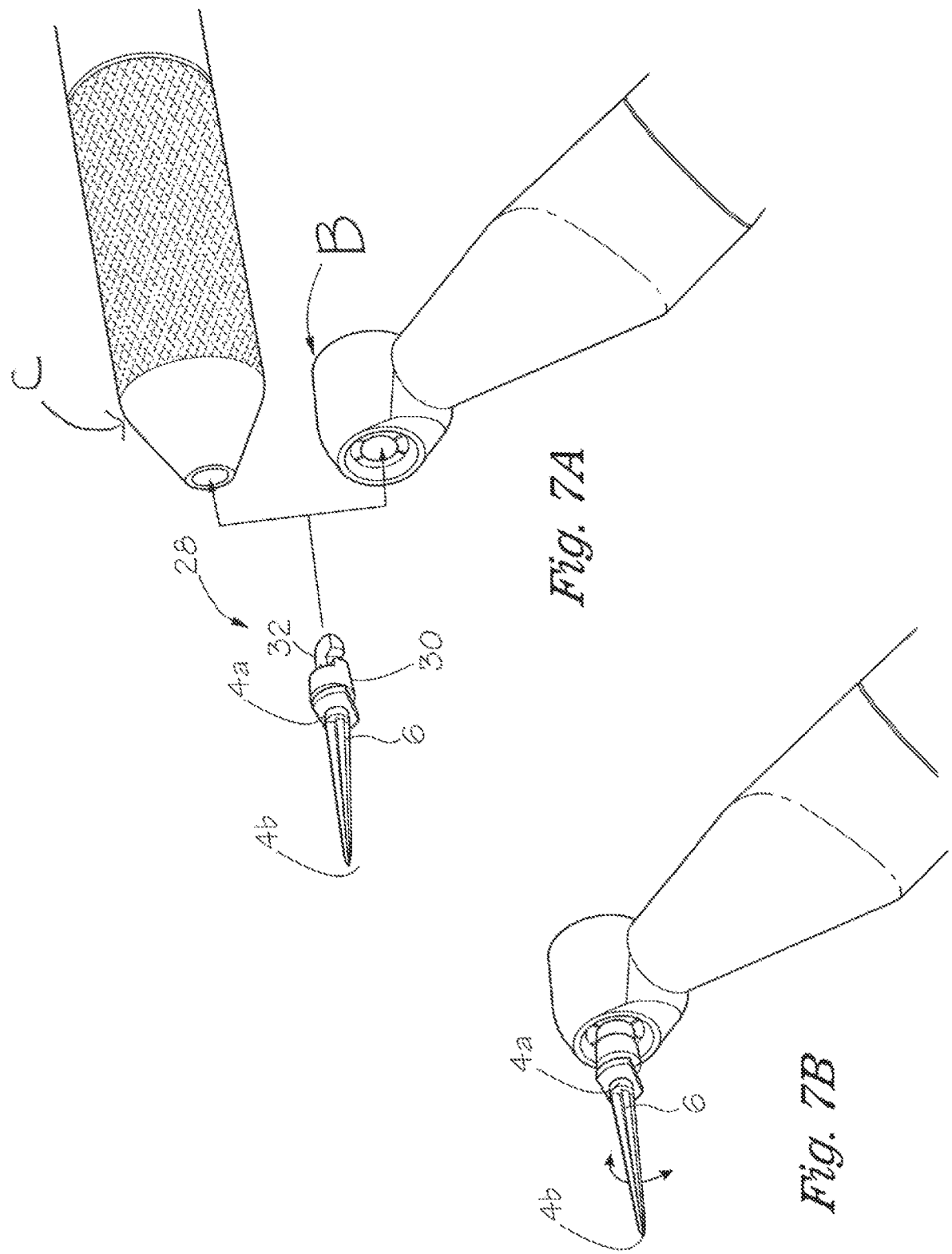

DENTAL CUTTING TOOL

BACKGROUND OF THE INVENTION

1) Field of the Invention

The present invention relates to an improved cutting tool for cutting openings in a patient's jaw so that a dental implant may be inserted into the opening. The invention includes a cutting blade that may be included as part of a hand-held tool or as an attachment to an electric drill.

2) Description of Related Art

Drill bits and cutting blades for use in the dental industry are commonly known. However, most of these drill bits and cutting blades are meant to be continuously rotated by an electric drill or hand tool. These bits and blades are not meant to be oscillated back and forth. As such, these bits and blades normally have cutting surfaces that oppose one another and/or are spread around the entire circumference of the bit so that as the bit or blade is rotated, each side of the bit may cut the bone to which the bit is being applied.

The prior art drill bits and cutting tools do not include a non-cutting, radiused surface that is opposite from the cutting surface(s) and can engage the bone so as to create a number of micro fractures in the bone, thereby making the bone more pliable. However, having a cutting tool that has such a radiused surface that is opposite from the cutting surface(s) is advantageous when cutting a dental implant opening where there is little bone that can receive and/or secure the implant in place. In such instances, there is no need to cut away bone from the opening's entire circumference but there is a need to cut bone from one surface (usually the palatal bone facing inwards towards the patient's throat) while also making at least one other surface of the surrounding bone (usually the facial bone facing outwards towards the patient's gums and lips) more pliable so that surrounding bone can more easily receive and secure the dental implant.

The prior art drill bits and cutting blades are often times cylindrical and do not taper towards a distal end. However, a tool having a cutting blade that tapers is advantageous when cutting an dental implant opening where there is little surrounding bone to receive and secure the implant. Such a tapered blade provides greater control over the size of the opening being cut as well as the amount of bone being fractured by the radiused surface.

Accordingly, it is an object of the present invention to provide a cutting tool having at least one cutting surface for cutting bone and one radiused surface for creating at least one fracture in the patient's bone.

Accordingly, it is an object of the present invention to provide a cutting tool where the cutting surface is generally opposite from the radiused surface.

Accordingly, it is an object of the present invention to provide a cutting tool wherein the cutting surface and the radiused surface are tapered.

SUMMARY OF THE INVENTION

The above objectives are accomplished according to the present invention by providing a cutting tool comprising: a proximal end having a cross sectional shape that is generally cylindrical; a distal end that forms a tapered point; a pick portion that extends between the proximal end and the distal end, the pick portion having a generally flat surface and a radiused surface so that the pick portion has a cross section that is generally semi-circular in shape, wherein the radiused surface is adapted to engage the surface of a bone and to create at least one micro fracture in the bone; a cutting blade extending along at least a portion of the generally flat surface of the pick portion and having a first side, a second side and a top interconnecting the first side and the second side, wherein each of the first side and the second side extend outwardly from the generally flat surface and have a concave surface; a first cutting edge defined by the first side and the top, wherein the first cutting edge is adapted to remove at least a portion of the patient's bone when the cutting blade engages the bone; and, whereby when the distal end is inserted into the patient's bone, a first portion of the patient's bone is engaged by the radiused surface while a second portion of the patient's bone is simultaneously engaged by the cutting blade so that when the proximal end is rotated, the radiused surface creates at least one micro fracture in the first portion of the patient's bone and the first cutting edge removes bone from the second portion of the patient's bone.

In at least one embodiment, the pick portion tapers as it extends from the proximal end to the distal end and the cutting blade tapers at the same rate as the pick portion when the cutting blade extends along at least a portion of the pick portion.

In another embodiment, the cutting tool further comprising a second cutting edge defined by the second side and the top of the cutting blade so that the second cutting edge is spaced from the first cutting edge by the width of the top of the cutting blade and when the distal end is inserted into the patient's bone, the first portion of the patient's bone is engaged by the radiused surface while the second portion of the patient's bone is simultaneously engaged by the cutting blade so that when the proximal end is rotated, the radiused surface creates at least one micro fracture in the first portion of the patient's bone and one of the first cutting edge and the second cutting edge removes bone from the second portion of the patient's bone.

In at least one embodiment, the width of the cutting blade tapers as the cutting blade extends along at least a portion of the pick portion so that the first cutting edge and the second cutting edge meet to form the tapered point at the distal end.

In one embodiment, the proximal end includes a connector that is adapted to be received by and secured to one of a hand operated handle and an electrically powered drill. In another embodiment, the proximal end is integral with a handle In one embodiment, the cutting blade is disposed on the pick portion such that the first portion of the patient's bone that is engaged by the radiused surface of the pick portion is spaced by approximately 180 degrees from the second portion of the patient's bone that is engaged by the cutting blade.

In another embodiment, the radiused surface is adapted to engage the surface of the bone and to apply uniform pressure on the bone when the proximal end is rotated so that the radiused surface creates at least one micro fracture in the bone.

BRIEF DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein:

FIG. 1 shows a side elevation view of the present invention.

FIG. 2 shows a close up view of a portion of the pick portion of the present invention having a cross sectional view of the cutting blade of the present invention.

FIG. 3 shows a cross sectional view of the cutting blade of the present invention.

FIG. 5 shows a perspective view of the present invention during use.

FIG. 6 shows a cross sectional view of the present invention during use.

FIGS. 7A-7B show a perspective view of the present invention being used with an electric drill and/or a hand operated handle.

Figure 4:
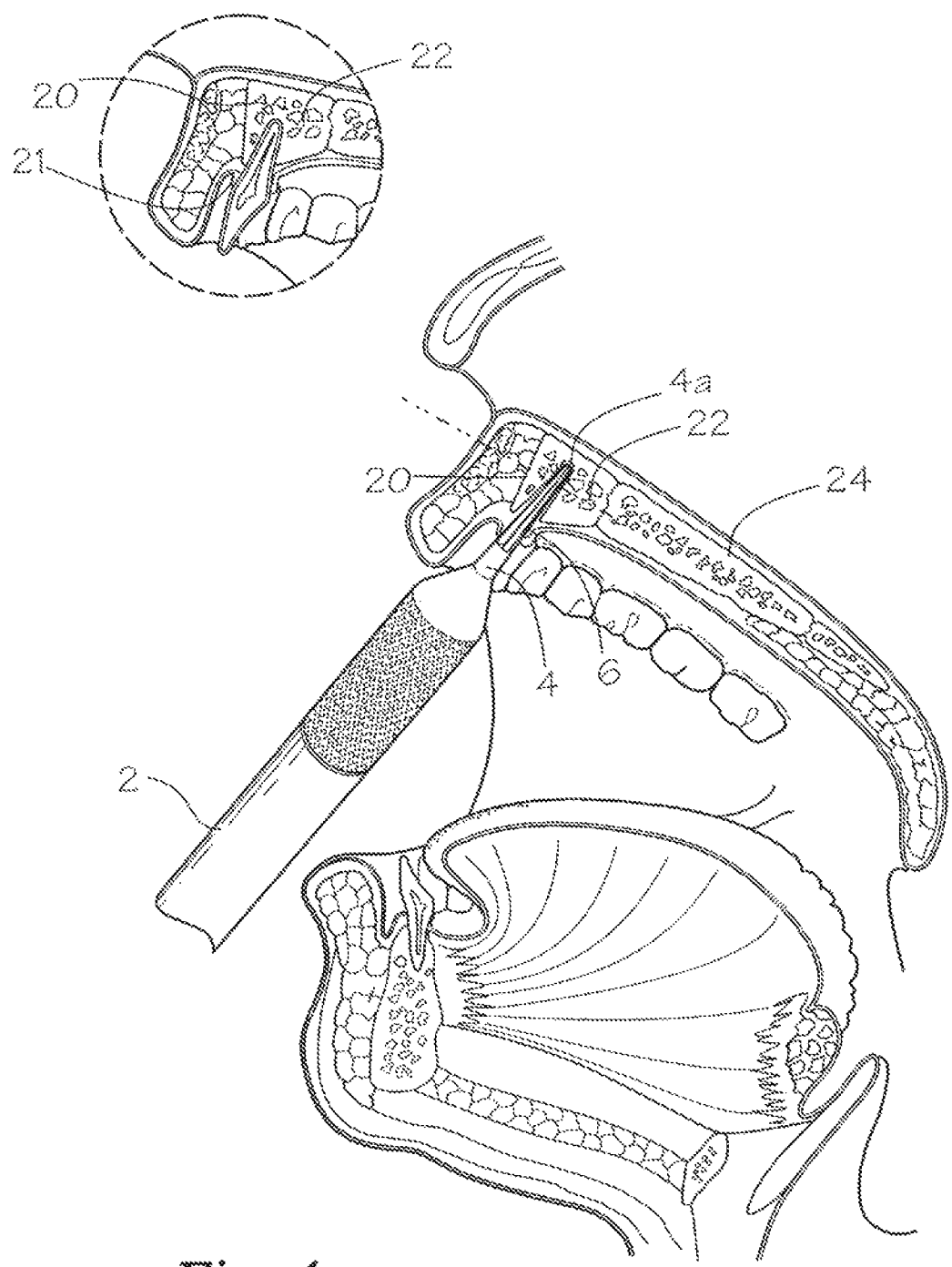
FIG. 4 shows a perspective view of the present invention during use.

It will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

DETAILED DESCRIPTION OF A PREFERRED EMBODIMENT

With reference to the drawings, the invention will now be described in more detail. Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are herein described.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

Referring now to FIGS. 1-3, the invention is generally shown as A. In one embodiment, the invention includes an elongated handle 2 which has a proximal end 2a that may be grasped by the user and a distal end 2b which carries a pick portion 4. The pick portion 4 has a proximal end 4a that is carried by the handle 2 and a distal end 4b that is used to penetrate and/or enter the patient's bone. At least part of the pick portion 4 has a generally flat surface 8a and 8b and a radiused surface 10 so that at least part of the pick portion 4 has a cross section that is generally semi-circular in shape (when viewed without reference to the cutting blade 6). In alternate embodiments, however, the flat surfaces 8a-8b could be angled in relation to one another, thus, giving the pick portion 4 a cross section that is generally pie shaped (when viewed without reference to the cutting blade 6). In the shown embodiment, the pick's proximal end 4a has a cross sectional shape that is generally cylindrical while the distal end 4b forms a tapered point. In alternate embodiments, however, proximal end 4a could have a cross section that is generally semicircular in shape (when viewed without reference to the cutting blade 6) and the distal end 4b could form a blunted, rounded end or having any number of cross sectional shapes. In other embodiments, the flat surface 8a-8b of the pick portion 4 could be slightly rounded or beveled.

The pick portion 4 further includes a cutting blade 6 that extends along at least a portion of the generally flat surface 8a and 8b of the pick portion 4 so that the cutting blade 6 is generally opposite from the radiused surface 10. The cutting blade 6 has a first side 12 and a second side 14, each of which extend outwardly and in a generally perpendicular direction from the flat surface 8a and 8b. The two opposing sides 12 and 14 are interconnected by a top surface 16. In the shown embodiment, each of the two sides 12 and 14 and the top 16 have a concave surface. The cutting blade 6 further includes a first cutting edge 18a and a second cutting edge 18b, wherein the first cutting edge is defined by the first side 12 and the top 16 and the second cutting edge is defined by the second side 14 and the top 16. The concave surface of the two sides and top 12, 14 and 16 are preferable and help define the first and second cutting edges 18a and 18b so that they have sharp edges but the concave surfaces are not necessary. In at least one embodiment, however, the top surface 16 is not concave. In other embodiments, neither of the two sides 14 and 16 nor the top 16 have a concave surface. In another embodiment, the top 16 has a concave surface but the two sides 14 and 16 do not.

In the shown embodiment, the pick portion 4 is generally tapered so that the diameter of the distal end 4b is less than the diameter of the proximal end 4a. In the shown embodiment, the cutting blade 6 is also tapered such that the width of the top surface 16 narrows as it approaches the distal end 4b of the pick portion 4. In the shown embodiment, the cutting edges 18a and 18b are angled towards one another as they extend from said proximal end 4*a* of the pick portion until they meet to form the tapered point at the distal end 4*b*. In alternate embodiments, however, the cutting blade 6 may maintain a uniform width despite the fact that the pick portion 4 tapers as it extends towards the distal end 4*b*. In such an embodiment, the cutting blade 6 may or may not extend all the way to the distal end 4*b*. In another embodiment, the cutting blade 6 may taper but the width of the top surface 16 of the cutting blade 6 may be such that the cutting edges 18*a*-18*b* do not meet at at a point adjacent to the distal end 4*b*. In yet another embodiment, the pick portion 4 does not taper at all as it extends from the proximal end 4*a* to the distal end 4*b*. In such an embodiment, the cutting blade 6 may or may not taper as it extends along the pick portion such that the width of the top surface 16 may (a) remain uniform to keep the cutting blades 18*a*-18*b* generally parallel to one another; or (b) decrease as the cutting blade 6 extends from the proximal end 4*a* to the distal end 4*b* so that the cutting blades 18*a*-18*b* meet at a point adjacent to the distal end 4*b*.

Referring now to FIGS. 4-6, the present invention can be seen while in use. The present invention is particularly useful in situations where there is very little surrounding bone into which a dental implant can be inserted. This can be the case where, for instance, the tooth was extracted or lost due to an abscess or other infection that ate away some of the bone surrounding the root socket. In such cases, there is often only a thin layer of facial bone 20 between the root socket 23 and the patient's gums/lips 21. However, there is often a much more palatal bone 22 between the root socket 23 and the roof of the patient's mouth 24.

After the original tooth has been extracted or otherwise lost by the patient, the distal end 4*b* of the pick portion 4 may be inserted into the remaining tooth socket 23. Because of the thinness and brittle nature of the facial bone 20, the distal end 4*b* will ordinarily be inserted so that the radiused surface 10 faces towards the patient's gums/lips 21 and, thus, engages the facial bone 20. This way, it will be less likely that a hole will be cut into or through the bone 20 as would likely be the case if the cutting blade 6 engaged the bone. The distal end being inserted as such, the cutting blade 6 will face and/or extend towards the roof of the patient's mouth 24 and will engage the palatal bone 22. Both the first and second cutting edges 18*a*-18*b* are adapted to remove at least a portion of the patient's bone when the pick portion 4 is inserted into the root socket 23 and the cutting blade 6 engages the bone.

Because the pick portion is tapered, it can be inserted into the root socket 23 at a depth where both the radiused surface 10 and the cutting blade 6 will simultaneously engage different sections of the patient's bone. Once the distal end 4*b* has been inserted to the proper depth within the root socket 23, pick portion 4 can be oscillated by rotating the handle 2 back and forth. When the handle is oscillated, a first section of the patient's bone (ordinarily 20) is engaged by the radiused surface 10 while a second section of the patient's bone (ordinarily 22) is simultaneously engaged by the cutting blade 6. When rotated, the radiused surface 10 creates a number of micro fractures in the first section of the patient's bone (ordinarily 20) so that the bone becomes more pliable and can more easily adapt to the shape of the dental implant being inserted. While the radiused surface 10 engages the first section of the bone, the first and second cutting edges 18*a*-18*b* may engage the second section of the patient's bone to remove some of the bone from the second section of the patient's bone. Alternatively, the pick portion can be inserted to a depth where either the radiused surface 10 or the cutting blade 6 (but not both) engage a section of the patients' bone. This may be desirable when no additional bone needs to be removed but a section of the patient's bone needs to be made more pliable by the radiused surface 10. Because, however, the radiused surface 10 is generally opposite from said cutting blade 6 and is preferably intended to engage a first section of bone (usually the facial bone 20) while the cutting blade simultaneously engages a second section of bone (usually the palatal bone 22), the pick portion is designed to be rotated by less than 360 degrees and preferably by 180 degrees or less. By limiting the range by which the pick portion 4 may be rotated, the likelihood that the cutting blade 6 will damage or otherwise cut the first section of bone (usually the facial bone 20) that is being fractured by the radiused surface 10 can be reduced, if not eliminated.

Referring now to FIGS. 7A-7B another embodiment of the invention can be seen wherein the proximal end 4*a* of the pick portion 4 includes a connector 28 that is adapted to be received by and removably secured to an electric drill B or a hand operated tool C. In this embodiment the connector 28 includes a connector stem 30 that includes a flat surface 32 that is formed in a portion of the connector stem 30. Once inserted into the hand operated tool or drill, the connector 26 may secure the pick portion 4 to the hand tool or drill so that the pick portion 4 can more easily be oscillated by either the hand tool or the electric drill.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art using the teachings disclosed herein.

What is claimed is:

1. A cutting tool comprising:
a proximal end having a cross sectional shape that is generally cylindrical;
a distal end;
a pick portion that extends between said proximal end and said distal end, said pick portion having a generally flat surface and a radiused surface extending outwardly from said generally flat surface, wherein said radiused surface is adapted to engage the surface of a bone and to create at least one fracture in the bone;
a cutting blade extending along at least a portion of said generally flat surface of said pick portion and having a first side, a second side and a top interconnecting said first side and said second side, wherein each of said first side and said second side extend outwardly from said generally flat surface and have a concave surface and wherein said top has a concave surface;
a first cutting edge defined by said first side and said top, wherein said first cutting edge is adapted to remove at least a portion of the patient's bone when said cutting blade engages the bone; and,
whereby when said distal end is inserted into the patient's bone, a first section of the patient's bone is engaged by said radiused surface while a second section of the patient's bone is simultaneously engaged by said cutting blade so that when said proximal end is rotated, said radiused surface creates at least one fracture in the first section of the patient's bone and said first cutting edge removes bone from the second section of the patient's bone.

2. The cutting tool of claim 1 wherein said pick portion tapers as it extends from said proximal end to said distal end and said distal end forms a tapered point.

3. The cutting tool of claim 2 wherein when said cutting blade extends along at least a portion of said pick portion, said cutting blade tapers at the same rate as said pick portion.

4. The cutting tool of claim 1 further comprising a second cutting edge defined by said second side and said top of said cutting blade so that said second cutting edge is spaced from said first cutting edge by width of said top of said cutting blade and when said distal end is inserted into the patient's bone, the first section of the patient's bone is engaged by said radiused surface while the second section of the patient's bone is simultaneously engaged by said cutting blade so that when said proximal end is rotated, said radiused surface creates at least one fracture in the first section of the patient's bone and one of said first cutting edge and said second cutting edge removes bone from the second section of the patient's bone.

5. The cutting tool of claim 4 wherein said width of said cutting blade tapers as said cutting blade extends along at least a portion of said pick portion so that said first cutting edge and said second cutting edge meet to form a tapered point at said distal end.

6. The cutting tool of claim 1 wherein said proximal end includes a connector that is adapted to be received by and secured to one of a hand operated handle and an electrically powered drill.

7. The cutting tool of claim 1 wherein said proximal end is integral with a handle.

8. The cutting tool of claim 1 wherein said distal end forms a tapered point.

9. A cutting tool comprising:
a proximal end having a connector that is adapted to be received by and secured to one of a hand operated handle and an electrically powered drill;
a distal end;
a pick portion that extends between said proximal end and said distal end, said pick portion including a generally flat surface and a radiused surface generally opposing said generally flat surface, wherein said radiused surface is adapted to engage the surface of a bone and to apply pressure on the bone so as to create at least one fracture in the bone;
a cutting blade extending along at least a portion of said generally flat surface of said pick portion, said cutting blade having a first side, a second side and a top portion interconnecting said first side and said second side, wherein each of said first side and said second side extend outwardly from said generally flat surface of said pick portion and each of said first side, said second side and said top portion have a concave surface;
a first cutting edge defined by said first side and said top portion, wherein said first cutting edge is adapted to remove at least a portion of the patient's bone when said cutting blade engages the bone;
a second cutting edge defined by said second side and said top portion, wherein said second cutting edge is adapted to remove at least a portion of the patient's bone when said cutting blade engages the bone; and, whereby when said distal end is inserted into the patient's bone, a first section of the patient's bone is engaged by said radiused surface while a second section of the patient's bone is simultaneously engaged by said cutting blade so that when said proximal end is rotated, said radiused surface creates at least one fracture in the first section of the patient's bone and one of said first cutting edge and said second cutting edge removes bone from the second section of the patient's bone.

10. The cutting tool of claim 9 wherein said cutting blade is disposed on said pick portion such that the first section of the patient's bone that is engaged by said radiused surface of said pick portion is spaced by approximately 180 degrees from the second section of the patient's bone that is engaged by said cutting blade.

11. The cutting tool of claim 9 wherein said pick portion tapers as it extends from said proximal end to said distal end.

12. The cutting tool of claim 11 wherein width of said top portion of said cutting blade tapers as said cutting blade extends along at least a portion of said pick portion so that said first cutting edge and said second cutting edge meet at said distal end.

13. A cutting tool comprising:
a proximal end;
a tapered distal end;
a tapered pick portion that extends between said proximal end and said distal end, said tapered pick portion includes a generally flat surface and a radiused surface extending outwardly from said generally flat surface, wherein said radiused surface is adapted to engage the surface of a bone and to create at least one fracture in the bone;
a cutting blade that extends along at least a portion of said generally flat surface of said pick portion, said cutting blade having a first side, a second side and a top portion interconnecting said first side and said second side, wherein each of said first side and said second side extend outwardly from said generally flat surface and has a concave surface and wherein said ton portion has a concave surface;
a first cutting edge defined by said first side and said top portion and a second cutting edge defined by said second side and said top portion, wherein each of said first cutting edge and said second cutting edge is adapted to remove at least a portion of the patient's bone when said cutting blade engages the bone; and, whereby when said distal end is inserted into the patient's bone, a first section of the patient's bone is engaged by said radiused surface while a second section of the patient's bone is simultaneously engaged by said cutting blade so that when said proximal end is rotated, said radiused surface creates at least one micro fracture in the first section of the patient's bone and one of said first cutting edge and said second cutting edge removes bone from the second section of the patient's bone.

14. The cutting tool of claim 13 wherein said cutting blade is disposed on said pick portion such that the first section of the patient's bone that is engaged by said radiused surface of said pick portion is spaced by approximately 180 degrees from the second section of the patient's bone that is engaged by said cutting blade.

15. The cutting tool of claim 13 wherein said proximal end includes a connector that is adapted to be received by one of a hand operated handle and an electrically powered drill.

16. The cutting tool of claim 13 wherein said proximal end is integral with a handle.

17. The cutting tool of claim 13 wherein said radiused surface is adapted to engage the surface of the bone and to apply uniform pressure on the bone when said proximal end is rotated so that said radiused surface creates at least one fracture in the bone.

18. The cutting tool of claim 13 wherein a width of said top portion of said cutting blade tapers along an entire length of said cutting blade so that said first cutting edge and said second cutting edge meet to form said tapered point at said distal end.

19. A cutting tool comprising:
a proximal end having a cross sectional shape that is generally cylindrical;
a distal end;
a pick portion that tapers as it extends between said proximal end and said distal end, said pick portion having a generally flat surface and a radiused surface extending outwardly from said generally flat surface, wherein said radiused surface is adapted to engage the surface of a bone and to create at least one fracture in the bone;
a cutting blade extending along at least a portion of said generally flat surface of said pick portion and having a first side, a second side and a top interconnecting said first side and said second side, wherein each of said first side and said second side extend outwardly from said generally flat surface and have a concave surface and wherein said cutting blade tapers along an entire length of said cutting blade;
a first cutting edge defined by said first side and said top, wherein said first cutting edge is adapted to remove at least a portion of the patient's bone when said cutting blade engages the bone; and,
whereby when said distal end is inserted into the patient's bone, a first section of the patient's bone is engaged by said radiused surface while a second section of the patient's bone is simultaneously engaged by said cutting blade so that when said proximal end is rotated, said radiused surface creates at least one fracture in the first section of the patient's bone and said first cutting edge removes bone from the second section of the patient's bone.

* * * * *

UNITED STATES PATENT AND TRADEMARK OFFICE
CERTIFICATE OF CORRECTION

| | |
|---|---|
| PATENT NO. | : 10,631,895 B2 |
| APPLICATION NO. | : 15/981964 |
| DATED | : April 28, 2020 |
| INVENTOR(S) | : Charles Buist, Sr. |

It is certified that error appears in the above-identified patent and that said Letters Patent is hereby corrected as shown below:

In the Claims

In Column 8, Line 37 of Claim 14, the word "ton" should be replaced with the word "top".

Signed and Sealed this
Twenty-eighth Day of July, 2020

Andrei Iancu
*Director of the United States Patent and Trademark Office*